United States Patent
Bundy et al.

(10) Patent No.: US 6,240,310 B1
(45) Date of Patent: May 29, 2001

(54) METHOD OF ACQUIRING MR DATA ESPECIALLY FOR CARDIAC CINE DATA SETS

(75) Inventors: Jeffrey M. Bundy; Orlando P. Simonetti, both of Naperville, IL (US)

(73) Assignee: Siemens Medical Systems, Inc., Iselin, NJ (US)

( * ) Notice: Subject to any disclaimer, the term of this patent is extended or adjusted under 35 U.S.C. 154(b) by 0 days.

(21) Appl. No.: 09/105,944

(22) Filed: Jun. 26, 1998

(51) Int. Cl.⁷ ................................................. A61B 5/055
(52) U.S. Cl. ........................... 600/420; 324/307; 324/309
(58) Field of Search .................................. 600/420, 410; 324/307, 309, 312

(56) References Cited

U.S. PATENT DOCUMENTS

| | | | |
|---|---|---|---|
| 4,710,717 | * 12/1987 | Pelc et al. | 324/309 |
| 4,939,463 | * 7/1990 | Sekihara et al. | 324/309 |
| 5,195,525 | * 3/1993 | Pelc | 128/653.2 |
| 5,251,628 | * 10/1993 | Foo | 128/653.2 |
| 5,474,067 | * 12/1995 | Laub | 128/653.2 |
| 5,653,233 | * 8/1997 | Pelc et al. | 128/653.2 |
| 5,692,508 | * 12/1997 | Simonetti et al. | 128/653.3 |
| 6,009,341 | * 12/1999 | Edelman | 600/413 |

* cited by examiner

*Primary Examiner*—Marvin M. Lateef
*Assistant Examiner*—Eleni Mantis Mercader
(74) *Attorney, Agent, or Firm*—Mark H. Jay

(57) ABSTRACT

During acquisition of one frame of MR data, the phase-encoding gradient oscillates between a maximum phase-encoding gradient and a minimum phase-encoding gradient. Each oscillation includes a zero phase-encoding gradient.

13 Claims, 3 Drawing Sheets

METHOD OF ACQUIRING MR DATA ESPECIALLY FOR CARDIAC CINE DATA SETS

BACKGROUND OF THE INVENTION

The invention relates to magnetic resonance (MR) imaging, and more particularly relates to cardiac MR studies of human patients. In its most immediate sense, the invention relates to acquisition of MR cardiac cine data sets for rapidly assessing the function of a human patient's left ventricle.

To make such an assessment, it is necessary to visualize the left ventricle and to distinguish the myocardium from the left ventricular blood pool during all phases of the cardiac cycle. Conventionally, this is done by acquiring a series of temporally spaced-apart images of the left ventricle (such a series of images is referred to as a "cine" acquisition). However, conventional cine acquisitions have a number of drawbacks.

One such drawback is that conventional cine acquisitions are slow. When using a conventional gradient-echo pulse sequence such as the two-dimensional FLASH pulse sequence that is presently implemented on the MAGNETOM® Vision MR imager manufactured by Siemens AG, a study to assess the function of the entire left ventricle can take 10 to 20 minutes to complete.

Another drawback is that a conventional cine acquisition can produce images of low quality. In a conventional cine acquisition, the images produced are actually composite images formed by combining information acquired during multiple cardiac cycles. Thus, the quality of the images produced by a conventional cine acqustion depends upon the degree to which the patient's cardiac rhythm remains invarient during the course of the acquisition. Additionally, if the acquisition takes place during free breathing, the heart moves together with the diaphragm. This results in blurring and image artifacts.

Although these drawbacks can be reduced by using various measures, such drawbacks have not been overcome. For example, image artifacts caused by respiration can be reduced by having the patient hold his or her breath and performing a cine acquisition for a single slice position within a single breath-hold using rapid image acquisition techniques. However, some patients are unable to hold their breath repeatedly, as they must do to acquire the necessary series of images. And, because assessment of the function of the entire left ventricle requires a series of breath-holds, changes in the patient's breath-hold positions will cause the images of the various slices to be misregistered.

Likewise, rapid two-dimensional gradient-echo techniques can produce a series of images in which each one is acquired fast enough to eliminate the effects of respiratory motion. However, due to the current limitations of gradient hardware the temporal resolution of these techniques is not adequate to assess changes in left ventricular function or wall motion.

Furthermore, known cine acquisition techniques require accurate and consistent ECG gating to produce adequate image quality and such gating is not always feasible. For example, the environment within the magnet of an MR imager is often unsuitable for establishing adequate ECG gating for cardiac patients. And, even when ECG gating is successful, arrhythmias can cause cycle-to-cycle variations in the MR signal, resulting in additional image artifacts.

It would therefore be advantageous to provide a method for conducting an MR study, and particularly a cardiac MR study for evaluating the function of a human patient's left ventricle, which could be completed rapidly, which could produce images of adequate quality, which would not require ECG gating, and which would not require multiple breath-holds.

The invention proceeds from the realization that spatial data can be shared from one image to the next to produce additional images and to therefore reduce the temporal spacing between images. (It is alreadly known to share data in some of the lines of the MR data or k-space matrix. The extra images thereby created have been called "echo-shared images". In the past, such echo-shared images have been generated only in combination with a segmented k-space acquisition.) The invention proceeds from the further realization that the each image, including the shared images, should include data not used in any other image, if each image is to provide unique information. The center line of the k-space matrix (i.e. the line of MR data acquired at a phase encoding of zero) is the line that provides the most MR signal for an image. Therefore, acquiring an additional center line for each image can efficiently provide unique information for each image, with a small increase in acquisition time. The invention still further proceeds from the realization that if there are large discontinuities in the MR data used to reconstruct an image, the image will contain artifacts. Therefore, it is necessary to make sure that such discontinuities do not arise.

In accordance with the invention, in addition to acquiring sufficient MR data to completely fill the k-space matrix for a particular image, one additional line of MR data is acquired. This line is the one acquired at a phase-encoding gradient of zero. This line is then, together with lines of data acquired for the current image and the next image, used to generate a new "shared" image. If the lines of MR data were to be acquired using a standard linear traversal through k-space, there would be a large discontinuity near the center of k-space due to motion occurring during the acquisition, and this discontinuity would cause artifacts in the shared image. Additionally, the k-space trajectory would be drastically different between the original images and the shared images. To avoid this discontinuity and this difference, the phase-encoding gradient is varied stepwise in a pattern that oscillates between a minimum and a maximum. Each oscillation (from minimum to maximum and from maximum to minimum) includes the acquisition of the zero phase-encoding line.

As will become evident below, such a data acquisition scheme allows many lines of MR data to be reused in reconstruction of multiple images. And, the time penalty caused by acquisition of additional lines of MR data at a zero phase-encoding is very small. In accordance with the preferred embodiment, MR data acquired during an interval of approximately 290 mS can be used to reconstruct 3.5 images, while a conventional image acquisition technique can only acquire enough data to reconstruct 2 images during that period of time. This improvement in temporal resolution provides adequate visualization of the function and the wall motion of the left ventricle.

In accordance with the preferred embodiment, a method in accordance with the invention is used in a gradient-echo MR pulse sequence in combination with a single breath-hold. In appropriate instances, a contrast agent may be administered to the patient and the acqustion of data may be gated to the patient's cardiac cycle.

BRIEF DESCRIPTION OF THE DRAWINGS

The invention will be better understood with reference to the accompanying exemplary and non-limiting drawings, in which.

DETAILED DESCRIPTION OF THE PREFERRED EMBODIMENTS

Figure 1:
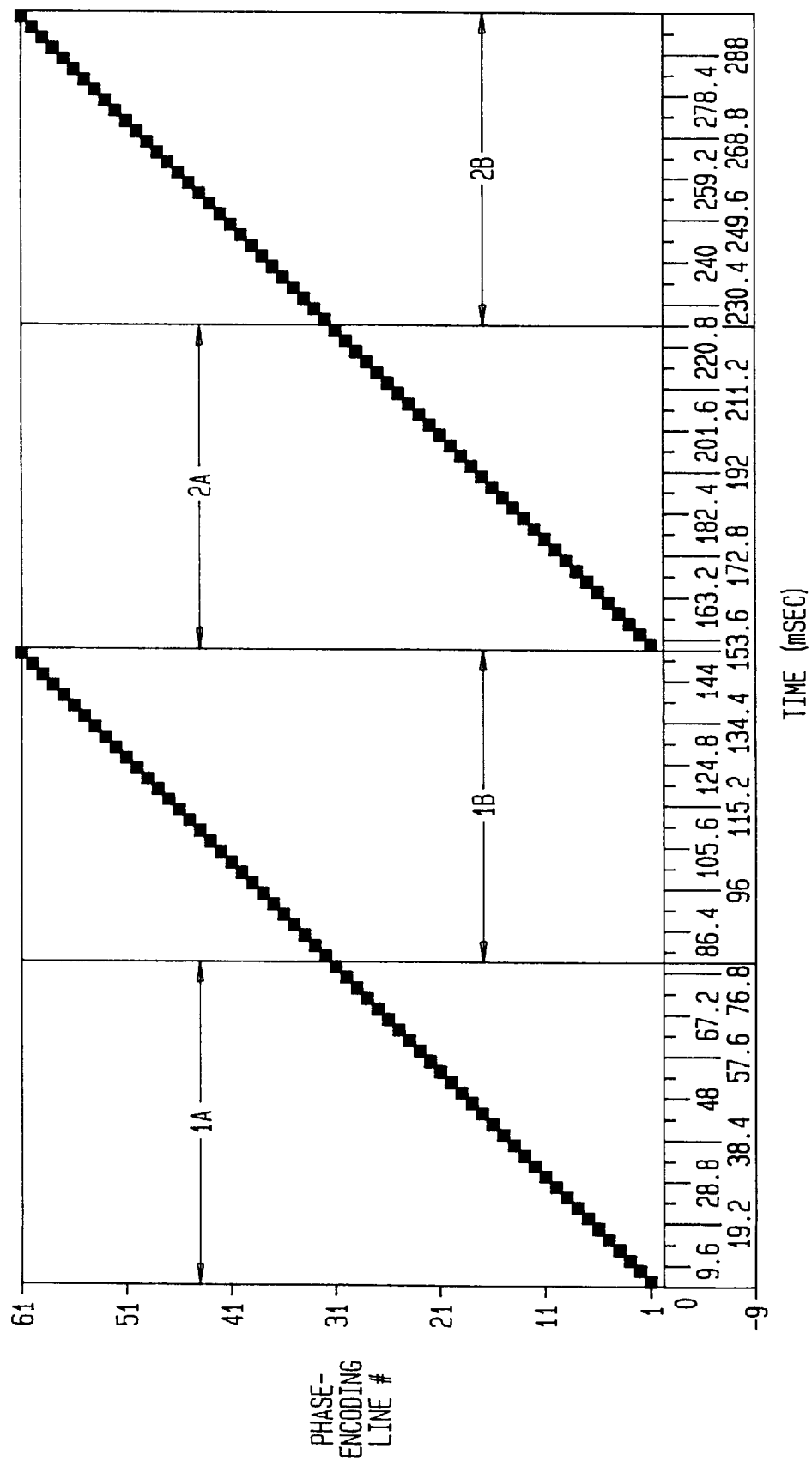
FIG. 1 shows variation of the phase-encoding gradient in a conventional gradient echo pulse sequence.

In a two-dimensional gradient echo MR pulse sequence such as the FLASH sequence marketed by Siemens AG as implemented on a 1.5 Tesla MAGNETOM Vision MR imager with TR=2.4 ms and TE=1.2 ms, each image is produced using a 61×128 k-space matrix, i.e. a matrix having 61 lines with 128 bits of information per line. Therefore, to form each MR image, MR data must be acquired at 61 phase-encoding gradient steps. Conventionally, the phase-encoding gradient begins at its most negative value (line 1 of the k-space matrix), steps up to a phase-encoding gradient of 0 (line 31 of the k-space matrix), and then continuest to step up until it reaches its most positive value (line 61 of the k-space matrix). Thereafter, the phase-encoding gradient begins once again at line 1 and progresses to line 61 as MR data for the next image is acquired. Because TR=2.4 ms, acquisition of each line of data takes place over 2.4 ms. And, each 61 line image takes 146.4 mS to acquire. This pattern is illustrated in FIG. 1, which illustrates the phase-encoding gradients used during the acquisition of two MR images. During period 1A, the phase-encoding gradient is stepped from its most negative value to zero (i.e. from line 1 to line 31 ); during period 1B, the phase-encoding gradient is stepped from the first value above zero to its most positive value (i.e. from line 32 to line 61). The MR data acquired during periods 1A and 1B are used to reconstruct a first MR image. Then, during period 2A, the phase-encoding gradient is stepped from its most negative value to zero (i.e. 31 lines of MR data are acquired to fill the first 31 lines of the k-space matrix); during period 2B, the phase-encoding gradient is stepped from the first value above zero to its most positive value (i.e.30 additional lines of MR data are acquired to fill the remaining lines of the k-space matrix). The MR data acquired during periods 2A and 2B are used to reconstruct a second MR image.

Figure 2:
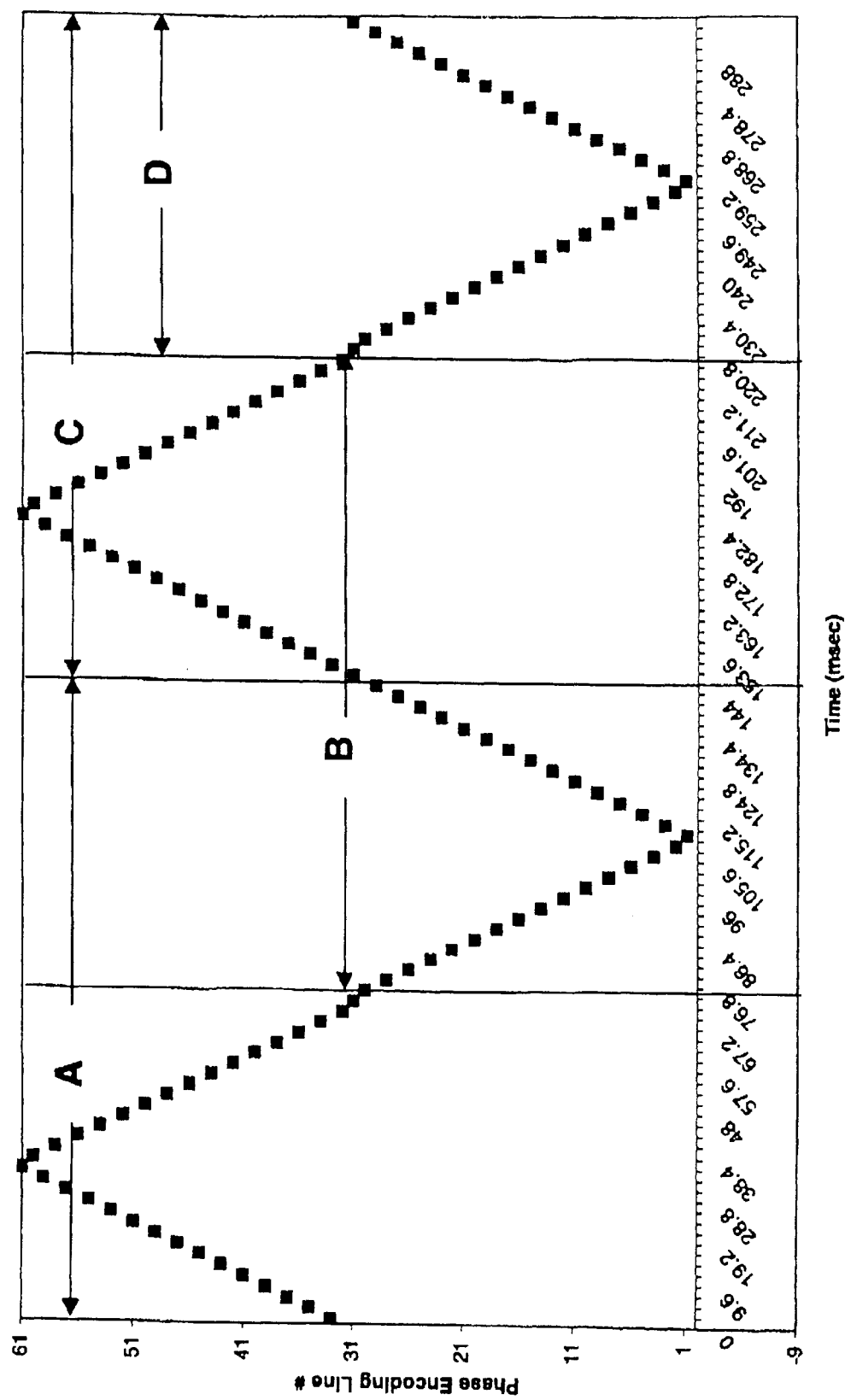
FIG. 2 shows variation of the phase-encoding gradient in a gradient echo pulse sequence in accordance with the preferred embodiment of the invention.

Although it would theoretically be possible to reconstruct a third MR image from the MR data acquired during periods 1B and 2A, such a reconstruction would contain artifacts because of the abrupt discontinuity in the MR data from which the third image would be reconstructed. As can be seen from FIG. 1, the last line acquired during period 1B is acquired at a maximum phase-encoding gradient and the first line acquired during period 2A is acquired at a minimum phase-encoding gradient. In accordance with the preferred embodiment of the invention as illustrated in FIG. 2, the phase-encoding gradient is varied stepwise in a pattern. The pattern oscillates between a maximum phase-encoding gradient and a minimum phase-encoding gradient. In each oscillation between the maximum and minimum phase-encoding gradients, the pattern includes a zero phase-encoding gradient.

Hence, as illustrated in FIG. 2, during acquisition of MR data the phase-encoding gradient is initially set to correspond to the phase-encoding gradient for line 33 of the above-referenced k-space matrix, 2 lines above the zero phase-encoding line (line 31 ). As MR data acquisition continues, the phase-encoding gradient is then stepped upward by a value corresponding to two lines of the above-referenced k-space matrix, i.e. lines 35, 37 . . . 61 are then acquired. Thereafter, as MR data acquisition continues, the phase-encoding gradient is stepped downward, and lines 60, 58, 56, 54 . . . 32 are acquired. At this point, instead of acquiring a line of MR data at a phase-encoding gradient of −1 (i.e. instead of acquiring line 30 of the k-space matrix next) an additional line of MR data is acquired at a phase-encoding gradient of zero. Hence, line. 31 of the k-space matrix is acquired immediately after line 32. Then, lines 30, 28, 26 . . . 8, 6, 4, and 2 are acquired.

Thereafter, line 1 of the k-space matrix is filled with MR data, and data acquisition continues as the phase-encoding gradient is stepped in two-line increments to acquire lines 3, 5, 7 . . . 31 . . . 57, 59, and 61 . The oscillation of the phase-encoding gradient continues as before, acquiring MR data in lines 60, 58, 56 . . . 32, 31, 30, 28, 26 . . . 4, and 2. This oscillatory pattern is then repeated.

It will be evident that between times T=0 and T=146.4 mS i.e. during period A as shown in FIG. 2, sufficient MR data have been acquired to fill all 61 lines of a 61×128 k-spaced matrix. The same is true between time T=74.4 mS and T=220.8 mS, i.e. during period B as shown in FIG. 2, and likewise during period C in FIG. 2. And, during period D in FIG. 2, sufficient MR data are acquired to fill ½ of a 61×128 k-space matrix. In other words, by using the preferred embodiment of the invention, it is possible to acquire sufficient data to reconstruct more than 3 MR images by adding only a few milliseconds to the time required to acquire MR data for only 2 MR images.

Although the preferred embodiment changes the phase-encoding gradient by an amount corresponding to two lines of a 61 line matrix in each step, this is not required. It would alternatively be possible to select a different step size and to therefore increase the number of oscillations required to fill up a single 61 line k-space matrix. Furthermore, use of a 61 line k-space matrix is not required; the size of the matrix can be chosen in accordance with the application intended.

In the preferred embodiment, the maximum phase-encoding gradient is positive and the minimum phase-encoding gradient is negative. This is preferred, but not required. It is alternatively possible to use a partial Fourier k-space matrix, which has lines corresponding to only some fraction greater than ½ of the lines used to reconstruct the image. The remaining lines are filled by interpolation or zero filling.

In the preferred embodiment, each MR image is reconstructed from MR data contained in a completely filled k-space matrix. This is advantageous, but not required. It is alternatively possible to acquire MR data in the center and at the extremes of the k-space matrix, but to omit one or more lines of MR data that are located elsewhere.

The preferred embodiment of the invention is particularly suitable for a cine acquisition of MR data from the human heart, and particularly (but not necessarily) for the acquisition of MR data from the left ventricle. Advantageously (but not necessarily), such an acquisition is carried out while the patient is holding his or her breath. This minimizes body motion that would otherwise occur during normal respiration. Further advantageously (but likewise not necessarily), an MR contrast agent such as Gd-DPTA is administered to the patient before or during the MR acquisition. This makes it easier to distinguish between the blood pool and the myocardium. Alternatively, the contrast agent could be an intravascular agent; in this instance, the MR acquisition could be carried out once the contrast agent had reached its equilibrium phase.

Figure 3:
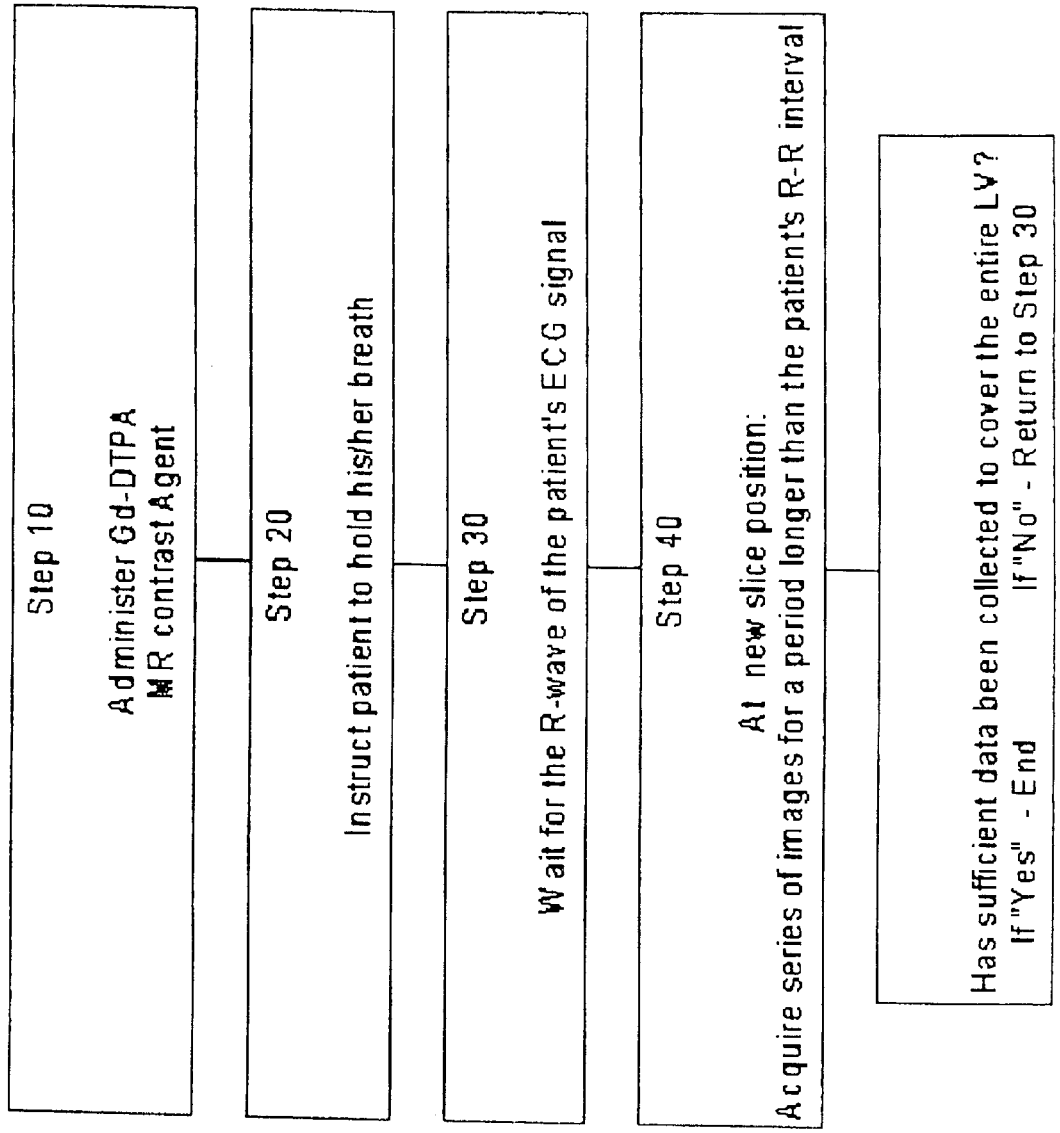
FIG. 3 is a flow chart of a preferred embodiment of the invention.

Hence, as is shown in FIG. 3, to evaluate the function of the left ventricle of the human heart, an MR contrast agent such as Gd-DTPA is administered to the patient (step 10). Then, in step 20, during the first pass of the contrast agent through the heart, the patient is instructed to hold his or her breath and the patient's EKG is monitored. In step 30, detection of an R wave is used to trigger acquisition of a single frame of MR data, relating to a corresponding slice of the left ventricle, taken parallel to the plane of the short axis of the left ventricle. (The slice could alternatively be taken parallel to the long axis of the left ventricle.)

During the acquisition (step 40), each frame of MR data is acquired while varying the phase-encoding gradient stepwise in a pattern that a) oscillates between a maximum phase-encoding gradient and a minimum phase-encoding gradient and that b) includes a zero phase-encoding gradient in each oscillation. Thereafter, and while the patient continues to hold his or her breath, this acquisition is repeated for a period longer than the patient's R—R interval, and then repeated again at new slice positions until a sufficient number of slices have been acquired to cover the entire left ventricle.

While one or more preferred embodiments have been described above, the scope of the invention is limited only by the following claims:

What is claimed is:

1. A method of conducting an MR study comprising the step of acquiring one frame of MR data while varying the phase-encoding gradient stepwise in a pattern that a) oscillates between a maximum phase-encoding gradient and a minimum phase-encoding gradient and that b) includes a zero phase-encoding gradient in each oscillation.

2. The method claim 1, wherein the zero phase-encoding gradient is included at the center of each oscillation.

3. The method of claim 1, wherein the stepwise variation equals two phase-encoding lines.

4. The method of claim 1, wherein the acquiring step comprises the step of using a gradient echo pulse sequence.

5. The method of claim 1, further comprising the step of reconstructing an MR image from the acquired MR data.

6. A method of conducting an MR study of the human heart, comprising the following steps:

instructing the patient to hold the patient's breath;

acquiring multiple frames of MR data while varying the phase-encoding gradient stepwise in a pattern that a) oscillates between a maximum phase-encoding gradient and a minimum phase-encoding gradient and that b) includes a zero phase-encoding gradient in each oscillation; and repeating said acquiring step in such a manner that upon each repetition, there is acquired a multi-frame sequence of MR data relating to a different slice of the heart.

7. The method of claim 6, further comprising the step of administering an MR contrast agent to the patient.

8. The method of claim 7, wherein the MR contrast agent is Gd-DPTA.

9. The method of claim 7, wherein the acquisition is conducted during the first pass of contrast agent through the heart.

10. The method of claim 7, wherein the MR contrast agent is an intravascular agent.

11. The method of claim 7, wherein the acquisition occurs during the equilibrium phase of an intravascular agent.

12. The method of claim 6, wherein the slices are taken parallel to the plane of an axis of the left ventricle of the patient's heart.

13. The method of claim 6, wherein the acquisition step is gated by the patient's EKG signal.

* * * * *